(12) United States Patent
Chung et al.

(10) Patent No.: US 12,000,793 B2
(45) Date of Patent: Jun. 4, 2024

(54) DISPOSABLE SELF-SENSING SIGNAL TEST STRIP AND ELECTROCHEMICAL SENSING METHOD THEREOF

(71) Applicant: UltraE Co. Ltd, Taichung (TW)

(72) Inventors: Hsieh-Hsun Chung, Taichung (TW); Ping-Hsi Hsieh, Taichung (TW)

(73) Assignee: ULTRAE CO. LTD, Taichung (TW)

( * ) Notice: Subject to any disclaimer, the term of this patent is extended or adjusted under 35 U.S.C. 154(b) by 197 days.

(21) Appl. No.: 17/575,970

(22) Filed: Jan. 14, 2022

(65) Prior Publication Data
US 2023/0228699 A1    Jul. 20, 2023

(51) Int. Cl.
*G01N 27/30* (2006.01)
*H04B 1/04* (2006.01)

(52) U.S. Cl.
CPC ............. *G01N 27/307* (2013.01); *H04B 1/04* (2013.01)

(58) Field of Classification Search
CPC . C12Q 1/00; C12Q 1/02; C12Q 1/006; C12Q 1/34; C12Q 1/54; G01N 27/327; G01N 27/3272; G01N 27/40; G01N 27/48; G01N 27/26; G01N 27/10; G01N 27/06; A61B 5/00; A61B 5/0022; A61B 5/7495
See application file for complete search history.

(56) References Cited

U.S. PATENT DOCUMENTS

2020/0008299 A1 *    1/2020    Tran .................... H05K 1/0386

FOREIGN PATENT DOCUMENTS

WO    WO-2013147351 A1 *    10/2013    ............. C12Q 1/001

OTHER PUBLICATIONS

English machine translation of WO-2013147351-A1 (Year: 2013).*

* cited by examiner

*Primary Examiner* — Gurpreet Kaur
(74) *Attorney, Agent, or Firm* — Muncy, Geissler, Olds & Lowe, P.C.

(57) ABSTRACT

A disposable self-sensing signal test strip includes a test strip body. The test strip body has a detection area and a circuit area. The detection area has a detection circuit. An electrochemical processing unit, a wireless transmission unit, and a power source unit are provided in the circuit area. The detection circuit is electrically connected to the electrochemical processing unit. The electrochemical processing unit sends to the detection circuit a control signal for performing detection. After receiving the control signal, the detection circuit reacts electrochemically with the test sample and sends a feedback signal to the electrochemical processing unit. The electrochemical processing unit converts the feedback signal into a detection parameter signal and sends the detection parameter signal through the wireless transmission unit to a receiving unit. The power source unit supplies electricity to the electrochemical processing unit and the wireless transmission unit.

2 Claims, 2 Drawing Sheets

DISPOSABLE SELF-SENSING SIGNAL TEST STRIP AND ELECTROCHEMICAL SENSING METHOD THEREOF

BACKGROUND OF THE INVENTION

1. Technical Field

The present invention relates to an electrochemical sensor test strip and its sensing method.

2. Description of Related Art

Electrochemical sensors have been maturely applied to the detection of various fluids. Existing electrochemical sensors have different configurations to meet different requirements, but their basic structures are more or less the same, including: a receptacle for receiving the fluid under test; a reagent for reacting electrochemically with an analyte in the fluid under test and generating an output signal associated with an electrical parameter; a plurality of electrodes, including a working electrode, a reference electrode, and a detecting electrode; and a measuring device for providing the necessary working voltage, receiving the output signal, and measuring a to-be-measured value that indicates the amount of the analyte.

In the prior art, the aforesaid reagent and detecting electrode typically coexist in the form of a sensor test strip, and the measuring device as a separate measuring instrument. To perform a detection operation, therefore, the operator must prepare the required measuring instrument(s) and sensor test strips that match the measuring instrument(s). Such preparation, however, can be inconvenient to the operator because different measuring instruments are required for different detection targets respectively. As measuring instruments are far pricier than sensor test strips, one who needs to detect multiple detection targets at the same time will be burdened by the lofty costs of the measuring instruments required, not to mention the inconvenience of having to carry those measuring instruments around if necessary.

The problems stated above have prevented extensive use of existing electrochemical sensors. Many potential users have chosen not to use electrochemical sensors simply considering their high selling prices, inconvenience of use, and portability issues.

BRIEF SUMMARY OF THE INVENTION

The primary objective of the present invention is to provide a sensor test strip and sensing method whose convenience of use is greatly enhanced in comparison with that of the prior art.

To achieve the foregoing and other objectives, the present invention provides a disposable self-sensing signal test strip that includes a test strip body. The test strip body has a detection area, which is designed for contact with a test sample, and a circuit area, which is not designed for contact with the test sample. The detection area has a detection circuit. The test strip body further has an electrochemical processing unit, a wireless transmission unit, and a power source unit, all of which are provided in the circuit area. The detection circuit is electrically connected to the electrochemical processing unit. The electrochemical processing unit is configured to send to the detection circuit a control signal for performing detection. The detection circuit is configured to react electrochemically with the test sample after receiving the control signal and send a feedback signal to the electrochemical processing unit. The electrochemical processing unit is further configured to convert the feedback signal into a detection parameter signal and send the detection parameter signal through the wireless transmission unit to a receiving unit that is not mechanically connected to the disposable self-sensing signal test strip. The power source unit is configured to supply electricity to the electrochemical processing unit and the wireless transmission unit.

To achieve the foregoing and other objectives, the present invention also provides a disposable self-sensing signal test strip that is composed essentially of a substrate, a detection circuit, an electrochemical processing unit, a wireless transmission unit, a power source unit, a protective layer, and a power source activation means. The substrate has a detection area, which is designed for contact with a test sample, and a circuit area, which is not designed for contact with the test sample. The detection circuit, the electrochemical processing unit, and the power soured unit are provided in the circuit area. The electrochemical processing unit is electrically connected to the detection circuit. The power source unit is configured to supply electricity to the electrochemical processing unit and the wireless transmission unit. The protective layer covers the circuit area, the electrochemical processing unit, the wireless transmission unit, and the power source unit completely. The power source activation means allows a user to selectively activate the ability of the power source unit to supply electricity to the electrochemical processing unit and the wireless transmission unit. In terms of operation, the electrochemical processing unit is configured to send to the detection circuit a control signal for carrying out detection. The detection circuit is configured to react electrochemically with the test sample after receiving the control signal and send a feedback signal to the electrochemical processing unit. The electrochemical processing unit is further configured to convert the feedback signal into a detection parameter signal and send the detection parameter signal through the wireless transmission unit to a receiving unit that is not mechanically connected to the disposable self-sensing signal test strip.

To achieve the foregoing and other objectives, the present invention further provides an electrochemical sensing method that uses either of the aforesaid disposable self-sensing signal test strips. The steps of the method are sequentially performed as follows:

To start with, the power source activation means is used to activate the ability of the power source unit to supply electricity to the electrochemical processing unit and the wireless transmission unit.

Then, the electrochemical processing unit sends to the detection circuit the control signal for carrying out detection.

After receiving the control signal, the detection circuit reacts electrochemically with the test sample and sends the feedback signal to the electrochemical processing unit.

The electrochemical processing unit converts the feedback signal into the detection parameter signal.

The electrochemical processing unit then sends the detection parameter signal through the wireless transmission unit to the receiving unit, which is not mechanically connected to the disposable self-sensing signal test strip.

According to the design described above, a user of the disposable test strip can use the test strip to generate and send out a detection parameter signal without having to resort to a measuring instrument. Moreover, the test strip can be directly used without having to be mechanically connected to external hardware equipment, and the selling price of the test strip can still be controlled to be much lower than an existing measuring instrument. Thus, the problems that have long hindered extensive use of electrochemical sensors are solved, allowing potential users to perform potentially required electrochemical detection operations (such as those related to health) at low cost.

DETAILED DESCRIPTION OF THE INVENTION

Figure 1:
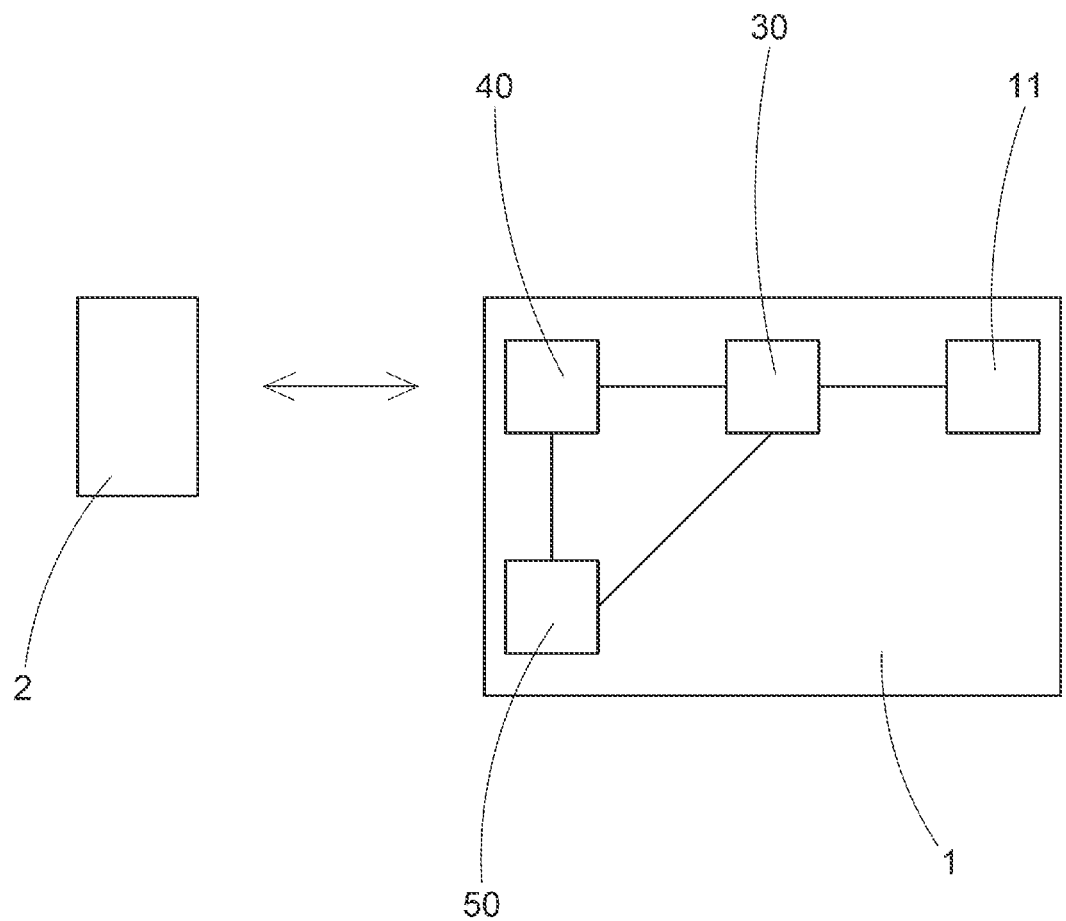
FIG. 1 is a block diagram of an embodiment of the present invention.
Figure 2:
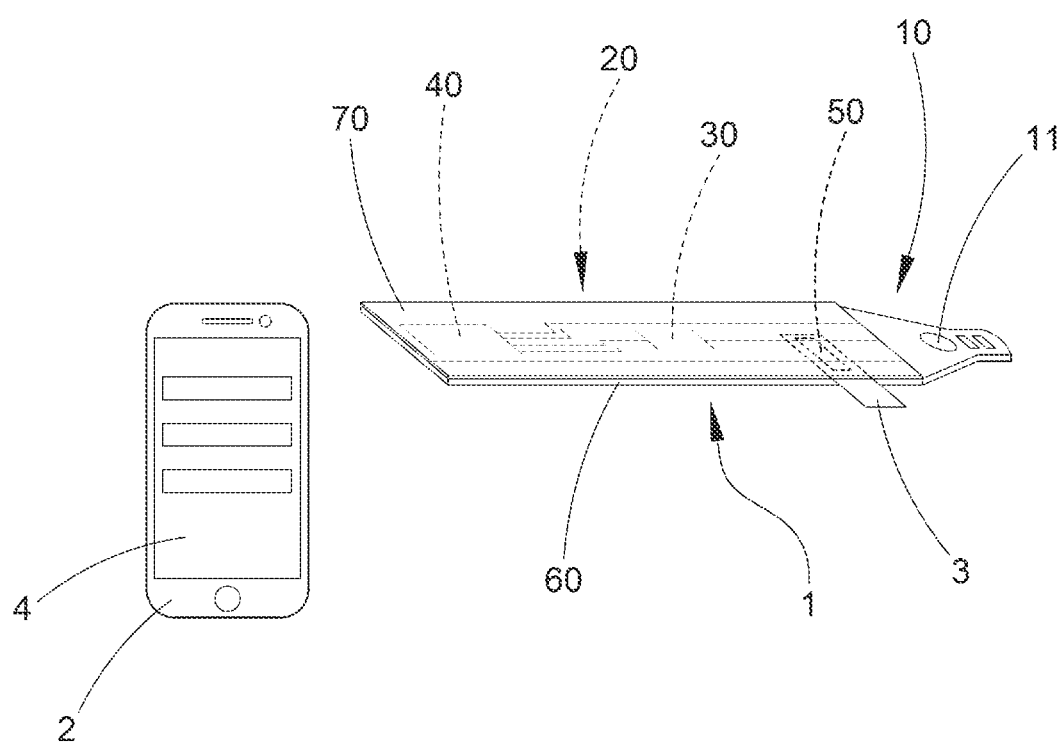
FIG. 2 is a schematic perspective view of the embodiment in FIG. 1.

Referring to FIG. 1 and FIG. 2 for an embodiment of the present invention, the disposable self-sensing signal test strip 1 can be used to detect various fluids, e.g., to detect the presence or absence of a target analyte in a test sample, the concentration of the target analyte if present, and/or other values to be detected. The test sample may be, but is not limited to, blood, urine, a water sample, or other non-water fluid samples. The target analyte may be, but is not limited to, glycosylated hemoglobin, blood sugar, a heavy metal, a nitrate, a nitrite, an allergen, formaldehyde, dissolved oxygen, or other compounds. The values to be detected may be, but are not limited to, pH values, electrical conductivity, or other physical parameters. The disposable self-sensing signal test strip 1 can be used in conjunction with a receiving unit 2 that is not mechanically connected to the disposable self-sensing signal test strip 1. The term "mechanically connected" refers to direct physical contact between two articles. The receiving unit 2 may be, but is not limited to, a mobile phone, a tablet computer, a regular computer, or other equipment that can be wirelessly connected to the disposable self-sensing signal test strip 1 and display, process, and/or perform relay transmission of detection parameter signals.

The disposable self-sensing signal test strip 1 includes a test strip body and a power source activation means 3. The test strip body has an electrochemical processing unit 30, a wireless transmission unit 40, a power source unit 50, a substrate 60, and a protective layer 70. The substrate 60 has a detection area 10 for contact with a test sample and a circuit area 20 not for contact with the test sample; in other words, each of the detection area and the circuit area exists as part of the test strip body. The detection area 10 has a detection circuit 11. The detection circuit 11 is electrically connected to the electrochemical processing unit 30. Depending on the target analyte or the value to be detected, the detection circuit 11 may include, for example but not limited to, a working electrode, a reference electrode, an auxiliary electrode, and/or a detecting electrode. Furthermore, depending on the target analyte or the value to be detected, at least a portion of the detection circuit 11 may additionally include, for example but not limited to, a reagent, enzyme, catalyst, and/or fermenting agent that is attached to an electrical conductor to help detect the target analyte or the value to be detected.

The electrochemical processing unit 30, the wireless transmission unit 40, and the power source unit 50 are provided in the circuit area 20. The protective layer 70 covers the circuit area 20, the electrochemical processing unit 30, the wireless transmission unit 40, and the power source unit 50 in their entirety. For example, the protective layer 70 is an electrical insulator and provides airtightness and/or watertightness. The electrochemical processing unit 30 may be, but is not limited to, a microprocessor. The wireless transmission unit 40 may be, but is not limited to, a Bluetooth transmission chip. The power source unit 50 is configured to supply electricity to the electrochemical processing unit 30 and the wireless transmission unit 40 and may be a capacitor, a fuel cell, or other rechargeable or non-rechargeable micro batteries. In one feasible embodiment, the disposable self-sensing signal test strip can be recycled after it is used for the first time; in particular, the rechargeable battery of the disposable self-sensing signal test strip can be recycled and used in a newly made or remade test strip body.

The power source activation means 3 allows a user to selectively activate the ability of the power source unit 50 to supply electricity to the electrochemical processing unit 30 and the wireless transmission unit 40. In other words, only when the electricity supplying ability of the power source unit 50 is activated can the power source unit 50 supply electricity to the electrochemical processing unit 30 and the wireless transmission unit 40. When the electricity supplying ability of the power source unit 50 is not activated, the power source unit 50 cannot supply electricity to the electrochemical processing unit 30 or the wireless transmission unit 40, and the electricity to be supplied is thus conserved. The power source activation means 3 is, for example, a plastic film capable of blocking the power source unit 50 from the other circuits and thereby depriving the power source unit 50 of its electricity supplying ability temporarily; when the plastic film is removed to allow electrical contact between the power source unit 50 and the other circuits, the electricity supplying ability of the power source unit 50 is restored. In other feasible embodiments, the power source activation means may be, but is not limited to, a switch or a rotary knob. In other feasible embodiments, the power source activation means is the action of placing the power source unit into the test strip body.

To lower the cost of the disposable self-sensing signal test strip, the disposable self-sensing signal test strip is particularly designed to exclude gold fingers with which to form mechanical connection with an external detection instrument, and a display for displaying detection parameter signals.

The disposable self-sensing signal test strip described above can be used in an electrochemical sensing method whose steps are sequentially performed as follows:

The power source activation means 3 is used to activate the ability of the power source unit 50 to supply electricity to the electrochemical processing unit 30 and the wireless transmission unit 40.

The electrochemical processing unit 30 then sends to the detection circuit 11 a control signal for carrying out detection.

After receiving the control signal, the detection circuit 11 reacts with the test sample electrochemically and sends a feedback signal to the electrochemical processing unit 30.

The electrochemical processing unit 30 converts the feedback signal into a detection parameter signal.

In addition, the electrochemical processing unit 30 sends the detection parameter signal through the wireless transmission unit 40 to the receiving unit 2, which is not mechanically connected to the disposable self-sensing signal test strip.

The detection parameter signal is then displayed by a display 4 of the receiving unit 2.

According to the design described above, a user of the disposable test strip can use the test strip to generate and send out a detection parameter signal without having to resort to a measuring instrument, and the detection parameter signal can be received and displayed by an existing personal device of the user's, such as a mobile phone or a tablet computer. Moreover, the test strip can be directly used without having to be mechanically connected to external hardware equipment, and the selling price of the test strip can still be controlled to be much lower than an existing measuring instrument. Thus, the problems that have long hindered extensive use of electrochemical sensors are solved, allowing potential users to perform potentially required electrochemical detection operations (such as those related to health) at low cost.

What is claimed is:

1. An electrochemical sensing method using a disposable self-sensing signal test strip comprising a test strip body having a detection area for contact with a test sample and a circuit area not for contact with the test sample, the detection area having a detection circuit, the test strip body further having an electrochemical processing unit, a wireless transmission unit, and a power source unit, wherein the electrochemical processing unit, the wireless transmission unit, and the power source unit are provided in the circuit area, the detection circuit is electrically connected to the electrochemical processing unit, and the power source unit is configured to supply electricity to the electrochemical processing unit and the wireless transmission unit, the disposable self-sensing signal test strip further comprising a power source activation means whereby a user is able to selectively activate an ability of the power source unit to supply electricity to the electrochemical processing unit and the wireless transmission unit of claim, the electrochemical sensing method comprising the steps, to be sequentially performed, of:

activating the ability of the power source unit to supply electricity to the electrochemical processing unit and the wireless transmission unit, by the power source activation means;

sending to the detection circuit, by the electrochemical processing unit, the control signal for performing the detection;

reacting with the test sample electrochemically, by the detection circuit after the detection circuit receives the control signal, and sending the feedback signal to the electrochemical processing unit by the detection circuit;

converting the feedback signal into the detection parameter signal by the electrochemical processing unit; and sending the detection parameter signal, by the electrochemical processing unit through the wireless transmission unit, to the receiving unit not mechanically connected to the disposable self-sensing signal test strip.

2. The electrochemical sensing method of claim 1, further comprising the step of:

displaying the detection parameter signal by a display of the receiving unit.

* * * * *